United States Patent [19]

Averill et al.

[11] Patent Number: 4,888,023
[45] Date of Patent: Dec. 19, 1989

[54] FEMORAL PROSTHESIS WITH UNCOUPLED DISTAL TIP

[75] Inventors: Robert G. Averill, Ringwood; Robert C. Cohen, Denville, both of N.J.

[73] Assignee: Osteonics Corp., Allendale, N.J.

[21] Appl. No.: 145,794

[22] Filed: Jan. 19, 1988

[51] Int. Cl.$^4$ .............................................. A61F 2/32
[52] U.S. Cl. ..................................................... 623/22
[58] Field of Search ................. 623/18, 19, 20, 21, 623/22, 23

[56] References Cited

U.S. PATENT DOCUMENTS

| | | | |
|---|---|---|---|
| 3,906,550 | 9/1975 | Rostoker et al. | 623/22 X |
| 4,406,023 | 9/1983 | Harris | 623/22 |
| 4,538,305 | 9/1985 | Engelbrecht et al. | 623/20 |
| 4,619,659 | 10/1986 | Witzel | 623/23 |
| 4,670,015 | 6/1987 | Freeman | 623/23 |
| 4,718,916 | 1/1988 | Morscher | 623/23 |
| 4,770,660 | 9/1988 | Averill | 623/23 |

FOREIGN PATENT DOCUMENTS 2538242  6/1984  France ................................ 623/23

Primary Examiner—Richard J. Apley
Assistant Examiner—David J. Bender
Attorney, Agent, or Firm—Samuelson & Jacob

[57] ABSTRACT

A stem-type femoral prosthesis has a distal tip with a fixation-resistant finish on the external peripheral surface of the distal tip so that the distal tip remains uncoupled from the femur upon implant of the prosthesis and during use. The distal tip is selectively removable and replaceable to enable a choice of size combinations in the joined stem and distal tip of the prosthesis for increased ease in the fitting of both the proximal and the distal portions of an appropriate prosthesis.

14 Claims, 1 Drawing Sheet

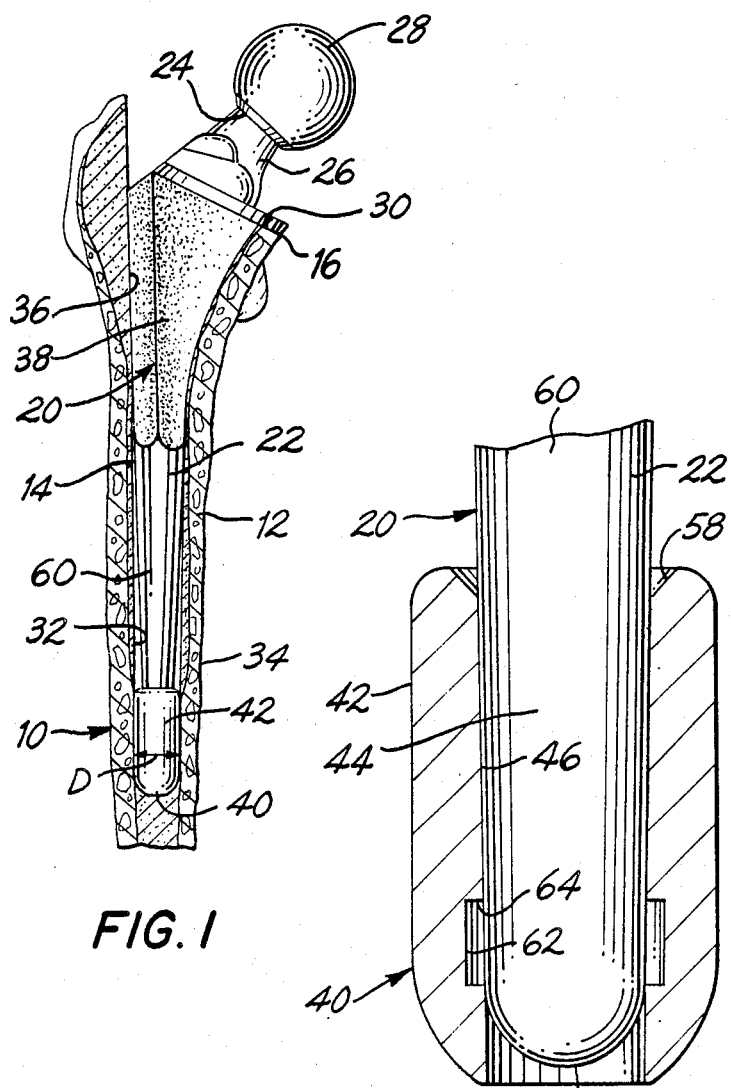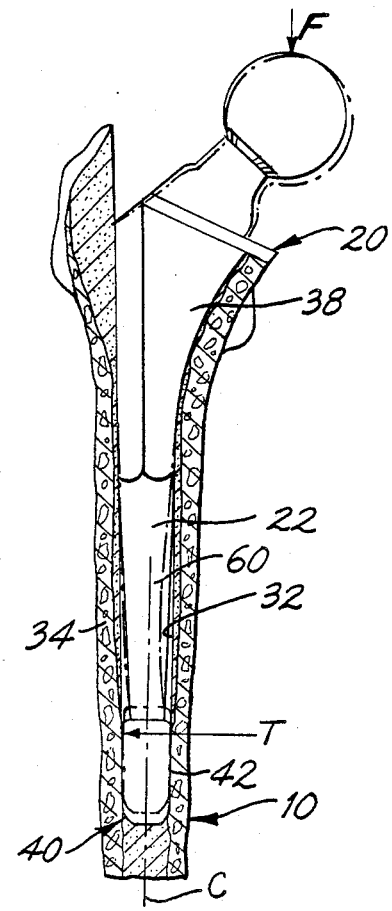
FIG. 1
FIG. 3
FIG. 2
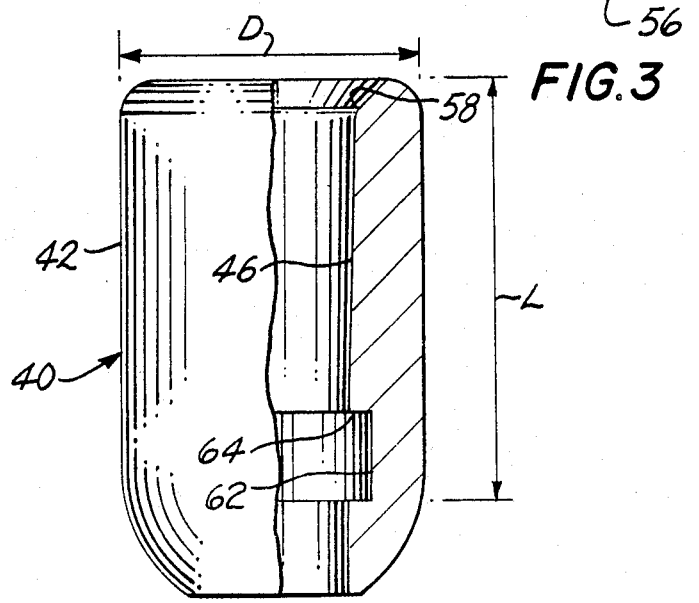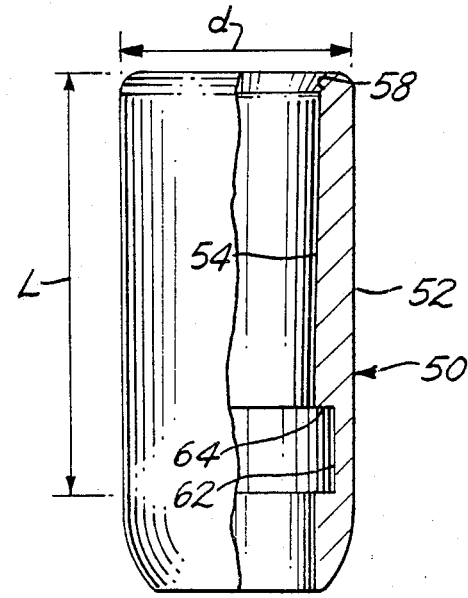
FIG. 4
FIG. 5

FEMORAL PROSTHESIS WITH UNCOUPLED DISTAL TIP

BACKGROUND OF THE INVENTION

The present invention relates generally to prosthetic implant devices and pertains, more specifically, to a femoral prosthesis of the type having a stem to be affixed within the femur for providing a ball at the proximal femur, with the stem extending longitudinally downwardly into the femur and terminating at a remote distal end of the stem.

Ordinarily, the implant of a femoral prosthetic device is accomplished by inserting the stem of the prosthesis longitudinally into a cavity formed in the prepared femur and affixing the stem, along at least a portion of the length thereof, within the cavity through the use of an interference fit or cement. In this manner, the stem of the device is coupled directly to the bone of the femur for securement and for the transmission of loads through the device to the femur. Because of the length of the stem, securement and load transmission are spread over a concomitant length of the femur, thereby reducing unit loads on the bone of the femur. Experience has shown that certain components of the forces exerted upon the prosthesis during use are transferred to distal portions of the stem, rather than being accommodated by proximal portions, with the result that higher stresses are present at corresponding nonproximal portions of the femur, while stresses at the proximal portions of the femur are reduced. For example, transverse forces on the ball of the prosthesis will tend to swing the prosthesis about the proximal end of the stem, thereby exerting bending stresses on the stem and establishing forces tending to move the distal end of the stem axially relative to the femur, as well as in a transverse direction. The affixation of the distal end of the stem to the femur resists such movement and stresses become concentrated at the affixed distal end. Excessive stress at that location can result in pain and can cause damage to the femur in the vicinity of the distal end of the stem of the prosthesis. In addition, where load is transferred away from the proximal end of the femur, a tendency arises for atrophy to take place at the proximal end, with a resultant loosening of the affixation of the proximal end of the stem, requiring early replacement of the entire prosthesis. The condition where stress tends to be concentrated at distal portions of the stem and reduced at proximal portions sometimes is referred to as stress shielding. Stress shielding is an undesirable condition which reduces or removes stresses from the proximal portions of the stem, which proximal portions are best able to accommodate the stress.

It has been suggested that stress shielding can be reduced, and even eliminated, through the employment of a sheath of synthetic resin material which receives the metallic stem of the prosthesis and is affixed within the femur such that the distal portion of the metallic stem can slide axially along the sheath in response to bending loads. As described in U.S. Pat. No. 4,619,659, the synthetic resin sheath is permanently implanted within the femur, and the metallic stem is releasably fitted into the sheath.

SUMMARY OF THE INVENTION

The present invention provides an improvement in a stem-type femoral prosthesis, which improvement deals with the problem of stress shielding in a simple, yet effective manner and accomplishes several objects and advantages, some of which may be summarized as follows: Provides control over the distribution of loads applied to the prosthesis so as to enable the transmission of axial and transverse forces to the femur at the most appropriate locations for better load distribution; precludes stress shielding and maintains at proximal portions of the femur those stresses which ordinarily are borne by the proximal portions of the femur; enables a more precise definition of the portions of the prosthesis selected to react with corresponding portions of the femur; provides an improved fit between the stem of the prosthesis and the femoral cavity and aids in centralizing the location of the distal end of the stem within the corresponding passage in the femur; permits the use of a more flexible stem, and a stem which transmits axial loads to the proximal femur while transferring bending moments to more distal portions of the femur; enables greater versatility in allowing the selection of a prosthesis of appropriate size from an offered range of sizes for increased ease and accuracy of fitting; facilitates the fitting of a prosthesis by enabling independent sizing at the proximal portion and the distal portion of the stem of the prosthesis; provides a wider range of choices of material and configuration in the design and construction of the stem of the prosthesis; reduces the number of individual component parts required in a complete prosthesis; simplifies implant procedures and subsequent removal, if necessary; and promotes superior performance over an extended service life.

The above objects and advantages, as well as further objects and advantages, are attained by the present invention which may be described briefly as an improvement in a stem-type femoral prosthesis for implantation in a resected proximal end of a femur, the prosthesis including a stem to be received within the prepared femur, the stem having a proximal end, an affixation surface adjacent the proximal end for enabling the stem to be affixed in place when seated properly within the prepared femur, and a distal end spaced axially downwardly from the proximal end for reception within a passage created in the wall of the prepared femur, the improvement comprising: a distal tip at the distal end of the stem, the distal tip being spaced axially downwardly from the affixation surface a distance sufficient to enable seating of the distal tip within harder portions of the bone in the wall of the femur when the affixation surface is properly seated in the prepared femur and having an external peripheral surface for engaging the harder portions of bone to confine the distal tip against transverse movements within the passage upon completion of the implantation, a fixation-resistant surface finish on the external peripheral surface for maintaining the distal tip unaffixed to the femur and moveable axially relative to the wall of the femur to permit axial displacement of the distal tip and the distal end in response to forces applied to the prosthesis during use of the prosthesis.

BRIEF DESCRIPTION OF THE DRAWING

The invention will be understood more fully, while still further objects and advantages will become apparent, in the following detailed description of preferred embodiments of the invention illustrated in the accompanying drawing, in which:

FIG. 1 is a partially cross-sectioned elevational view showing a prosthesis incorporating the improvement of the present invention implanted within a resected femur;

FIG. 2 is diagrammatic outline drawing of the illustration of FIG. 1, exaggerated somewhat to demonstrate operation of the improvement;

FIG. 3 is an enlarged fragmentary cross-sectional view of a portion of FIG. 1;

FIG. 4 is an elevational view, partially sectioned, of a component part of the present invention; and FIG. 5 is an elevational view, partially sectioned, of an alternate component part of the present invention.

DESCRIPTION OF THE PREFERRED EMBODIMENTS

Referring now to the drawing, and especially to FIG. 1 thereof, the proximal end of a femur 10 has been resected for the implant of a femoral prosthesis. Femur 10 includes an outer shell of cortical bone 12, inner cancellous bone 14 and calcar 16. A femoral prosthesis employing the improvement of the present invention is illustrated at 20 and is shown implanted at the prepared proximal end of the femur 10.

Femoral prosthesis 20 is of the type having a stem 22 which is inserted into the prepared proximal portion of the femur 10 to be affixed to the femur 10 so that a prosthetic portion 24 which is unitary with the stem 22 at the proximal end of the stem 22 of the prosthesis will provide a neck 26 upon which is placed a spherical head 28 for engagement with either the natural acetabulum or an acetabular prosthesis for articulation in a hip replacement. The femur 10 is prepared to receive prosthesis 20 by cutting to establish a neck resection level at 30 and then creating a passage 32 within the wall 34 of the femur 10 as a part of a cavity 36 in the prepared femur 10 for receiving the stem 22 of the prosthesis 20. The distal end of the stem 22 is inserted into passage 32 and advanced axially downwardly until the stem 22 is seated fully within the passage 32. Upon proper seating of the prosthesis 20 in the cavity 36 of the prepared femur 10, an affixation surface 38 on the prosthesis 20, adjacent the proximal end of the stem 22, is seated in cavity 36 in appropriate position for affixation of the proximal portion of the stem 22 to the corresponding proximal portion of the femur 10.

A distal tip 40 is located at the distal end of the stem 22, spaced axially downwardly from the affixation surface 38, so as to extend downwardly into passage 32 and be positioned so that distal tip 40 is seated within harder portions of the bone of the wall 34 of femur 10, namely, within either dense cancellous bone or cortical bone, when the affixation surface 38 is seated properly within the cavity 36. Distal tip 40 has a generally cylindrical external peripheral surface 42 extending along a major portion of the length of the distal tip 40, and the external peripheral surface 42 has a diameter D complementary to the diameter of the portion of the passage 32 within which the distal tip 40 is seated so that the external peripheral surface 42 engages the harder portions of the bone of the wall 34 of the femur 10 to be confined against transverse movements within the passage 32 upon completion of the implantation. The external peripheral surface 42 is provided with a fixation-resistant surface finish so that the distal tip 40 will not be affixed to the wall 34 of the femur 10 and will remain unaffixed to the femur 10 during use of the prosthesis 20. Distal tip 40 is constructed of a bio-compatible material, one such material being a cobalt-chrome steel alloy, and the fixation-resistant finish on the external peripheral surface 42 is a very smooth surface finish, such as that which is attained by polishing and buffing the cobalt-chrome steel alloy.

Upon completion of the implant, stem 22 is seated within cavity 36 and is affixed to the femur 10 at affixation surface 38. As best seen in FIG. 2, a force applied to the prosthesis during use, such as illustrated by force F, will transmit load to the femur 10 itself through the affixation at affixation surface 38 at the proximal portion of the stem 22. Bending moments established by the tendency for prosthesis 20 to swing about the proximal portion of the stem 22 in response to the application of force F will result in the transmission of transverse forces, such as force T, to more distal, nonproximal portions of the femur 10, at the distal tip 40. At the same time, these bending moments will tend to displace the distal tip 40 axially upwardly along the passage 32, as shown in phantom in FIG. 2. Since the distal tip 40 is not affixed to the wall 34 of the femur 10, such axial displacement is permitted, while the close fit of the distal tip 40 in the passage 32 assures the desired transmission of the transverse force T to the femur 10. The axial upward displacement of the distal tip 40 as illustrated in phantom in FIG. 2 is exaggerated for illustrative purposes, as is the bending of the stem 22. Where force F is oriented so that bending moments are reduced, axial displacement of distal tip 40 within passage 32 can be in an axially downward direction, as a result of compression of the bone of the femur 10. The cylindrical configuration of the external peripheral surface 42 permits rotational displacement of the distal tip 40 about the central axis C thereof within passage 32 relative to the wall 34 of femur 10 in response to torsional forces. If the distal tip 40 were to be affixed to the wall 34 of the femur 10, the coupling of the distal end of the stem 22 at the distal tip 40 could result in stress shielding, by virtue of the shifting of the load from the proximal portion of the stem 22 to the distal portion. The uncoupling of the distal tip 40, and the distal end of the stem 22, from the wall 34 of the femur 10 precludes such stress shielding and the concomitant deleterious effects of stress shielding.

Distal tip 40 is integral with the distal end of the stem 22 so that all movements of the distal end of stem 22 result in corresponding movements of the distal tip 40. While distal tip 40 may be made unitary with stem 22, it is preferable that distal tip 40 be removable selectively from stem 22. Turning now to FIG. 3, distal tip 40 is shown to be a separate component part fitted onto distal end portion 44 of the stem 22. To this end, distal end portion 44 is tapered and distal tip 40 is provided with a central bore 46 having a taper complementary to the taper on distal end portion 44 so that by merely slipping the central bore 46 over the distal end portion 44, the distal tip 40 is secured to the distal end of stem 22. In order to release the distal tip 40, one need merely pull the distal tip 40 from the distal end portion 44 with a force sufficient to release the grip exerted by the engaged complementary tapers. Securing means in the form of engaged tapered surfaces are well known, one of the more common forms being known as the Brown and Sharpe taper connection. Thus, distal tip 40 is selected from a series of distal tips offered in a range of outside diameters so that a surgeon may choose the diameter for external peripheral surface 42 appropriate for the size of the passage 32 into which the distal tip 40 will be fitted.

As illustrated in FIG. 4, as well as in FIG. 1, the diameter D of the external peripheral surface 42 of the distal tip 40 matches the inside diameter of passage 32, so that the distal tip 40 centers the stem 22 within the passage 32 and locates the stem 22 positively within the passage 32. An alternate distal tip 50 is illustrated in FIG. 5 and is seen to have an external peripheral surface 52 with a diameter d smaller than the diameter D of distal tip 40. However, the dimensions of the central bore 54 of distal tip 50 are the same as the central bore 46 of distal tip 40, so that either of the distal tips 40 or 50 may be selected for securement to the stem 22, utilizing the same securement mechanism, to match the diameter of the passage 32 in the prepared femur 10. Conversely, for any diameter passage 32, the size of the prosthesis 20 to be fitted into the passage 32 may be varied and the proper seating of the stem 22 in the passage 32 is assured by the selection of a distal tip of appropriate size. In this manner, fitting of an appropriate prosthesis 20 is facilitated since a wide variety of size combinations is made available in the joined stem and distal tip to provide independent sizing of the proximal portion and the distal portion of the stem without the necessity for maintaining on hand a large inventory of completed prosthetic devices. Securement is facilitated by the rounded configuration 56 at the distal end of the stem 22 and the chamfer 58 provided at the opening to the central bore of the distal tip.

Once secured, the distal tip 40 engages the passage 32 along the external peripheral surface 42, which external peripheral surface 42 is long enough to maintain a relatively low stress on the wall 34 of the femur 10 at the more distal portions of the femur 10 in the vicinity of the distal tip 40. Thus, the length L of the cylindrical portion of external peripheral surface 42 is long enough to provide sufficient contact area between the distal tip 40 and the wall 34 of the femur 10 to reduce the stress along that contact area to a manageable level. The external peripheral surface 52 of distal tip 50 is provided with a similar length L. However, length L is short enough to preserve flexibility in the shaft 60 of the stem 22, which shaft 60 is the portion of the stem 22 extending between the affixation surface 38 and the distal tip 40. Flexibility in the shaft 60 enables the stem 22 to respond in the manner illustrated in FIG. 2 so that the combination of the prosthesis 20 and the femur 10 can manage the forces to be applied to the prosthesis 20. It is desirable that the shaft 60 have sufficient flexibility to preclude excessive stiffening of the femur 10 by the prosthesis 20 along the implant site. In the preferred configuration, the diameter of the shaft 60 of the stem 22 above the distal tip is made smaller than the diameter of the external peripheral surface of the distal tip itself so as to render the shaft 60 flexible, while still providing a contact area between the distal tip and the wall of the femur great enough to maintain relatively low contact stresses.

Should it become necessary to remove prosthesis 20 after some period of use, such removal is facilitated by the ability of the distal tip 40 to move axially within the passage 32. Since the fixation-resistant surface finish on the external peripheral surface 42 of the distal tip 40 will discourage fixation of the distal tip 40 within the passage 32 as a result of ingrowth, withdrawal of the stem 22 from the passage 32 ordinarily is accomplished with ease. However, in the event that tissue growth has been able to impede the withdrawal of the distal tip 40, as for example by filling in tissue in the passage 32 immediately above the distal tip 40, and the impediment is sufficient to resist withdrawal of the distal tip 40 with the stem 22, the securement means provided by the tapered interconnection along the tapered distal end portion 44 of the stem 22 will release the distal tip 40 from the stem 22 so that the stem still can be withdrawn readily. The distal tip 40 has an internal annular groove 62 which provides a generally radial shoulder 64 facing downwardly, so as to confront the lowermost end of the distal tip 40, which shoulder 64 serves as a purchase for an extraction tool (not shown) which the surgeon can insert into the central bore 46 of the released distal tip 40 to grasp the distal tip 40 and withdraw the distal tip from the passage 32. As seen in FIG. 3, the axial extent and location of the groove 62 is such that the groove 62 is closed off by the stem 22 when the distal tip 40 is secured to the distal end portion 44 of the stem, so as to assure that the shoulder 64 is isolated from passage 32 and is maintained clear for any subsequent use. Distal tip 50 has a like groove 62 and shoulder 64 in the wall thereof.

Thus, it can be seen that the improvement of the present invention provides for the accurate location of the distal end of the stem 22 of the prosthesis 20, centralized within the passage 32, and fitted closely in the passage, for better fit, better load distribution with a specifically defined area over which load is transferred to the femur 10, and for the prevention of stress shielding. Increased flexibility is enabled in the stem 22 itself, thereby permitting better management of the loads distributed to the femur. The ability to remove and replace the distal tip 40 with another distal tip selected from distal tips offered in a range of sizes enables greater versatility in fitting in that a wide variety of size combinations is made available in the joined stem and distal tip so as to enable independent sizing at the proximal portion and at the distal portion of the stem without multiplying the number of stems needed to achieve such versatility. In providing such modularity between the stem and the distal tip, a greater choice is made available in the materials selected for the stem, as well as for the distal tip, so that the stem can be made even more flexible for better accommodation of loads during use. In addition, should it become necessary to remove and replace the prosthesis 20, such replacement is facilitated by the unaffixed, uncoupled distal tip.

It is to be understood that the above detailed description of preferred embodiments of the invention are provided by way of example only. Various details of design and construction may be modified without departing from the true spirit and scope of the invention as set forth in the appended claims.

The embodiments of the invention in which an exclusive property or privilege is claimed are defined as follows:

1. In a stem-type femoral prosthesis for implantation in a resected proximal end of a femur, the prosthesis including a stem to be received within the prepared femur, the stem having a proximal end, an affixation surface adjacent the proximal end for enabling the stem to be affixed in place when seated properly within the prepared femur, and a distal end spaced axially downwardly from the proximal end for reception within a passage created in the wall of the prepared femur, the improvement comprising: a distal tip integral with the distal end of the stem, the distal tip being spaced axially downwardly from the affixation surface a distance sufficient to enable seating of the distal tip within harder portions of the bone in the wall of the femur when the affixation surface is properly seated in the prepared femur, the stem including a shaft portion located between the affixation surface and the distal tip, the shaft portion having a diameter smaller than the corresponding diameter of the distal tip for enabling flexing in the shaft portion, and the distal tip having an external peripheral surface for engaging said harder portions of bone to confine the distal tip against transverse movements within the passage upon completion of the implantation, and a fixation-resistant surface finish on the external peripheral surface for maintaining the distal tip unaffixed to the femur and moveable axially relative to the wall of the femur to permit axial displacement of the distal tip and the distal end in response to forces applied to the prosthesis during use of the prosthesis.

2. The improvement of claim 1 wherein the external peripheral surface of the distal tip has an axial length long enough to provide an area of contact between the distal tip and the wall of the femur, when the stem is seated properly in the passage, to maintain a relatively low level of stress on the wall of the femur at the location of the distal tip in response to forces applied to the prosthesis which result in transverse forces at the distal tip.

3. The improvement of claim 2 wherein the external peripheral surface is cylindrical such that the distal tip is rotatable about the central axis thereof relative to the wall of the femur.

4. The improvement of claim 1 including securing means for securing the distal tip to the stem for selective removal and replacement of the distal tip.

5. The improvement of claim 4 wherein the securing means includes a securing mechanism responsive to relative axial movement between the stem and the distal tip for securing and releasing the distal tip and the stem.

6. The improvement of claim 5 including a generally radial shoulder on the distal tip, the shoulder confronting the lowermost end of the distal tip for providing a purchase for an extractor tool.

7. The improvement of claim 6 wherein the securing mechanism includes an internal bore in the distal tip and complementary tapered surfaces on the stem and on the internal bore of the distal tip, the internal bore including an annular groove and the shoulder being located within the annular groove, and the annular groove being placed axially such that upon engagement of the complementary tapered surfaces the stem will close off the annular groove and isolate the shoulder from the passage.

8. The improvement of claim 5 wherein the securing mechanism includes an internal bore in the distal tip and complementary tapered surfaces on the stem and on the internal bore of the distal tip.

9. The improvement of claim 8 wherein the external peripheral surface of the distal tip includes means in the form of an axial length long enough to provide an area of contact between the distal tip and the wall of the femur, when the step is seated properly in the passage for maintaining a relatively low level of stress on the wall of the femur at the location of the distal tip in response to forces applied to the prosthesis which result in transverse forces at the distal tip.

10. The improvement of claim 9 wherein the external peripheral surface is cylindrical such that the distal tip is rotatable about the central axis thereof relative to the wall of the femur.

11. The improvement of claim 1 wherein the fixation-resistant finish is a smooth finish on the external peripheral surface of the distal tip.

12. The improvement of claim 11 wherein the distal tip is constructed of a metal alloy and the fixation-resistant finish comprises a polished surface.

13. The improvement of claim 1 wherein the external peripheral surface of the distal tip includes means in the form of an axial length long enough to provide an area of contact between the distal tip and the wall of the femur, when the stem is seated properly in the passage, for maintaining a relatively low level of stress on the wall of the femur at the location of the distal tip in response to forces applied to the prosthesis which result in transverse forces at the distal tip, and the external peripheral surface is cylindrical such that the distal tip is rotatable about the central axis thereof relative to the wall of the femur.

14. The improvement of claim 13 wherein the fixation-resistant finish is a smooth finish on the external peripheral surface of the distal tip.

* * * * *

REEXAMINATION CERTIFICATE (2782th)
United States Patent [19]
Averill et al.

[11] B1 4,888,023
[45] Certificate Issued Jan. 23, 1996

[54] FEMORAL PROSTHESIS WITH UNCOUPLED DISTAL TIP

[75] Inventors: Robert G. Averill, Ringwood; Robert C. Cohen, Denville, both of N.J.

[73] Assignee: Osteonics Corp., Allendale, N.J.

Reexamination Request:
No. 90/003,379, Mar. 30, 1994

Reexamination Certificate for:
Patent No.: 4,888,023
Issued: Dec. 19, 1989
Appl. No.: 145,794
Filed: Jan. 19, 1988

[51] Int. Cl.[6] .................................................. A61F 2/32
[52] U.S. Cl. ............................................................ 623/22
[58] Field of Search ............................ 623/16, 18, 19, 623/20, 22, 23

[56] References Cited

U.S. PATENT DOCUMENTS

| | | | |
|---|---|---|---|
| 3,793,650 | 2/1974 | Ling et al. | 3/1 |
| 4,589,883 | 5/1986 | Kenna | 623/22 |

FOREIGN PATENT DOCUMENTS

| | | | |
|---|---|---|---|
| 0158534 | 10/1985 | European Pat. Off. | A61F 2/36 |
| 0179626 | 4/1986 | European Pat. Off. | A61F 2/30 |
| 2247721 | 4/1974 | Germany | A61F 1/100 |
| 8226978 | 1/1984 | Germany . | |
| 1409053 | 10/1975 | United Kingdom | A61F 1/100 |
| 2153233 | 8/1985 | United Kingdom | A61F 2/28 |
| 8302555 | 8/1983 | WIPO | A61F 1/100 |

OTHER PUBLICATIONS

Whiteside Product Literature, Dow–Corning Wright Journal of Bone & Joint Surgery, vol. 68–A, Jan. 1986.
Mecron Product Literature, Mecron Medical Products, Inc. Journal of Bone & Joint Surgery, vol. 68–A, Dec. 1986.
Dick et al. "Experiences with the Development of Non–Cemented Prostheses", *Medizinische–Orthopädische Technik*, Jan. 1986, pp. 6–10 (with translation).
Freeman Product Literature, Corin Medical Ltd. Journal of Bone & Joint Surgery, vol. 68–B, Jan. 1986.
Exeter Product Literature, Howmedica, Journal of Bone and Joint Surgery, vol. 64–A, Apr. 1982.
Exeter Product Literature (brochure), Howmedica, Dec. 1981.
Lee "Total Hip Prosthesis: Mechanics of Evolution of Optimal Design"; *Biomechanics of Medical Devices*, Ghista, ed.; Marcel Decker, N.Y. 1981 pp. 325–369.

*Primary Examiner*—David J. Isabella

[57] ABSTRACT

A stem-type femoral prosthesis has a distal tip with a fixation-resistant finish on the external peripheral surface of the distal tip so that the distal tip remains uncoupled from the femur upon implant of the prosthesis and during use. The distal tip is selectively removable and replaceable to enable a choice of size combinations in the joined stem and distal tip of the prosthesis for increased ease in the fitting of both the proximal and the distal portions of an appropriate prosthesis.

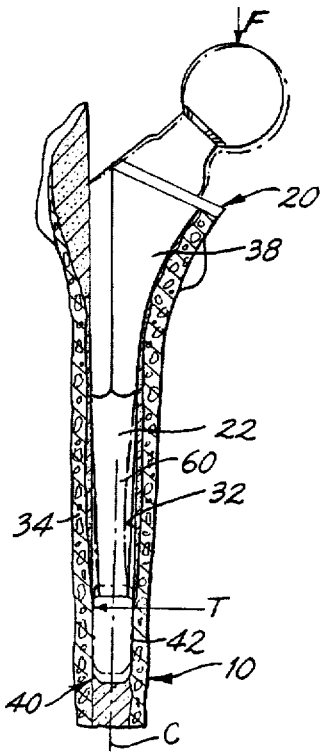

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–14 is confirmed.

* * * * *